United States Patent [19]

King et al.

[11] Patent Number: 4,503,079
[45] Date of Patent: Mar. 5, 1985

[54] PROCESS FOR THE MANUFACTURE OF ETHYL ALCOHOL FROM CITRUS MOLASSES

[75] Inventors: Donald W. King, Maitland, Fla.; Terrance M. Placzek, Hallam, Nebr.

[73] Assignee: A. Duda and Sons, Inc., Oviedo, Fla.

[21] Appl. No.: 453,736

[22] Filed: Dec. 27, 1982

[51] Int. Cl.³ .................... A23K 1/02; C12P 7/12
[52] U.S. Cl. .................... 426/54; 426/494; 435/164
[58] Field of Search ........... 426/54, 494, 425, 476, 426/387; 435/161, 164, 165, 276, 819

[56] References Cited

U.S. PATENT DOCUMENTS

| 963,275 | 7/1910 | Chute | 435/161 |
|---|---|---|---|
| 2,148,051 | 2/1939 | Talladas | 426/15 |
| 2,534,341 | 12/1950 | Cross | 426/387 |
| 2,561,072 | 7/1951 | Reich | 435/164 |
| 2,631,103 | 3/1953 | Kermer | 426/387 |
| 2,956,887 | 10/1960 | Lund | 426/476 |
| 2,984,601 | 5/1961 | Sudarsky | 435/276 |
| 3,112,248 | 11/1963 | Sudarsky | 435/267 |
| 3,461,035 | 8/1969 | Sellers | 435/244 |
| 4,046,789 | 9/1977 | Muller | 426/425 |
| 4,309,254 | 1/1982 | Dahlstrom | 426/494 |
| 4,310,629 | 1/1982 | Muller | 435/162 |
| 4,316,956 | 2/1982 | Lutzen | 435/161 |
| 4,321,328 | 3/1982 | Hoge | 435/161 |

FOREIGN PATENT DOCUMENTS

| 0458025 | 7/1949 | Canada | 435/164 |
|---|---|---|---|
| 1909901 | 9/1970 | Fed. Rep. of Germany | 426/210 |
| 2042514 | 3/1972 | Fed. Rep. of Germany | 426/54 |
| 3025098 | 1/1981 | Fed. Rep. of Germany | 435/161 |
| 0864177 | 3/1961 | United Kingdom | 426/387 |

OTHER PUBLICATIONS

Uzdennikov, Effect of Some Terpenes on Bacteria, Fungi and Protozoa, 1972 Chem. Abst., vol. 78, 1973 p. 86.

Akimov et al., Antimicrobial Activity of Terpenes from *Juniperus sabina* L. 1977, Chem. Abst., vol. 86, 1977, p. 101.

Food Industries Manual, 20th ed. 1970, "Sulphiting" p. 181, Ed. by Woollen, Chem. Publ. Co., N.Y.

Primary Examiner—Robert Yoncoskie
Assistant Examiner—Marianne S. Minnick
Attorney, Agent, or Firm—Julian C. Renfro

[57] ABSTRACT

The invention relates to a process for the production of ethyl alcohol from citrus molasses fermentation in which improved yields of ethyl alcohol are obtained by preliminarily removing fermentation inhibiting agents, specifically oils, from the fermenter charge. The process may be carried out in batch or by continuous operation. The alcohol formed in the fermentation step is distilled off at about 190° proof and the latter may then be dehydrated in a molecular sieve column to produce a product substantially free of water. Also a novel oil stripper is presented in order that the oils may be effectively and economically removed prior to fermentation.

8 Claims, 2 Drawing Figures

FIG. 1

PROCESS FOR THE MANUFACTURE OF ETHYL ALCOHOL FROM CITRUS MOLASSES

BACKGROUND OF THE INVENTION

It is well known that when citrus fruit is processed to produce juices for packaging, canning, or concentration, citrus waste residue remains. This residue is useful in that it contains oils, fermentable substances and nutritional material useful as an animal feed.

Citrus molasses is made from the citrus waste residue by treating the residue with lime to facilitate the release of bound juices. The citrus waste residue is then heavily pressed to expel the juices which are usually concentrated to a syrup in the industry.

The term citrus molasses as used herein will be construed to mean the expelled juices from citrus waste residue and not be limited only to the concentrated syrup product. In reference to a citrus waste residue, this may be obtained from various citrus fruits of commercial value, for example oranges, grapefruit, lemons and limes.

Citrus molasses typically will contain 9% to 15% soluble solids of which 60% to 70% are sugars. This corresponds to a Brix of between 6° and 12.5° and a moisture content of 90%. Total volatile compounds of 88.39% to 94.36% are typical. Citrus molasses contains sugars that are convertible to ethyl alcohol by yeast fermentation, but also contains non-fermentable sugars and substances that inhibit fermentation. Due to a lack of recognition of the presence of these inhibitors, or to an inability to remove them economically, the prior attempts to obtain ethyl alcohol from citrus wastes could not be economically justified.

The U.S. patent to Reich, U.S. Pat. No. 2,561,072 taught the partial concentration of citrus waste liquors followed by subjecting the partially concentrated liquors to alcoholic fermentation, evaporatively concentrating the fermented liquors, and separating alcohol from the vapors of the second concentration step. Citric acid was separated from the final concentrate, and the residue from the separation was able to be dried and utilized as an industrial product.

In one of the Reich embodiments, the process was carried out utilizing multiple-stage evaporation for preliminarily and finally concentrating the waste citrus liquors. However, we have found that the use of evaporator systems to volatilize the oils and concentrate the molases were not energy efficient, nor effective for satisfactory oil removal, and the capital costs were quite large. It was to overcome the shortcomings of these and other such systems that the present process was evolved.

SUMMARY OF THIS INVENTION

Citrus molasses as prepared from citrus waste products contains not only fermentable sugars, but also substances that act to inhibit fermentation, specifically the oils present in citrus molasses. We have found that improved yields of ethyl alcohol are obtained if we remove a major amount of the essential oils prior to fermentation. This is accomplished in the preferred embodiment of our process by the utilization of a steam stripping operation. The stripped molasses, together with recycled process liquors and water is forwarded to a fermentation procedure using fresh and recycled yeast. Following the fermentation, the fermented mixture is distilled to remove the alcoholic component as the principal product. The distillate is dehydrated, preferably by the use of a molecular sieve (a crystalline metal alumino silicate) to substantially anhydrous ethyl alcohol. The spent beer from the distillation step is split, a portion being recycled to the fermentation step, and the remainder is forwarded to be dried for the production of a nutritious animal feed.

In order to remove the inhibiting ingredients in the most effective manner, we heat the citrus molasses, and under negative pressure conditions, the citrus molasses is sparged with steam, thus facilitating the stripping, condensing and decanting of the citrus oil which inhibits fermentation. Citrus stripper oil is comprised of a substantial amount of d-limonene, and mono-cyclic terpene, which is a potent bacteriostatic agent. A corresponding concentration of the citrus molasses occurs during the stripping of the oil by the vaporization of moisture and of volatile compounds from the molasses. The molasses is also sterilized of any microbial growth that could lower fermentation yields. The concentrated molasses is then diluted with a combination of recycled process liquor and fresh water, resulting in a balanced solution of fermentable sugars from citrus molasses. Since oils that inhibit alcohol recovery have been removed during our distillation procedure, we can manufacture ethyl alcohol from citrus molasses on a manifestly profitable basis.

The principal object of this invention is thus to provide a highly fermentable citrus molasses for fermentation to ethyl alcohol.

A further object of the invention is to provide a process for the effective removal of essential oils from citrus molasses prior to fermentation for the production of ethyl alcohol.

Another object of the invention is to provide a process for the continuous fermentation of citrus molasses to ethyl alcohol.

Yet another object is to provide a process to dehydrate the produced ethyl alcohol to an anhydrous state (198+ proof) by contacting the product with an adsorbent material having an affinity for water.

Still another object is to concentrate the spent beer stream by providing a process of evaporation by waste-heat activated vapor recompression for the evaporation of moisture and the recovery of nutritional solids which can be used as animal food.

Yet still another object is to provide a novel oil separator device able to be operated on a substantially continuous basis to accomplish the removal of certain oils from citrus molasses, such that the de-oiled molasses can then be fermented on an economical basis to form ethyl alcohol.

These and other objects, features and advantages will be more apparent as the description proceeds.

BRIEF DESCRIPTION OF DRAWINGS

FIG. 1 is a schematic view illustrating the principal components utilized in our novel process, with arrowheads being utilized in order to show flow directions.

PROCESS DESCRIPTION

Figure 1:
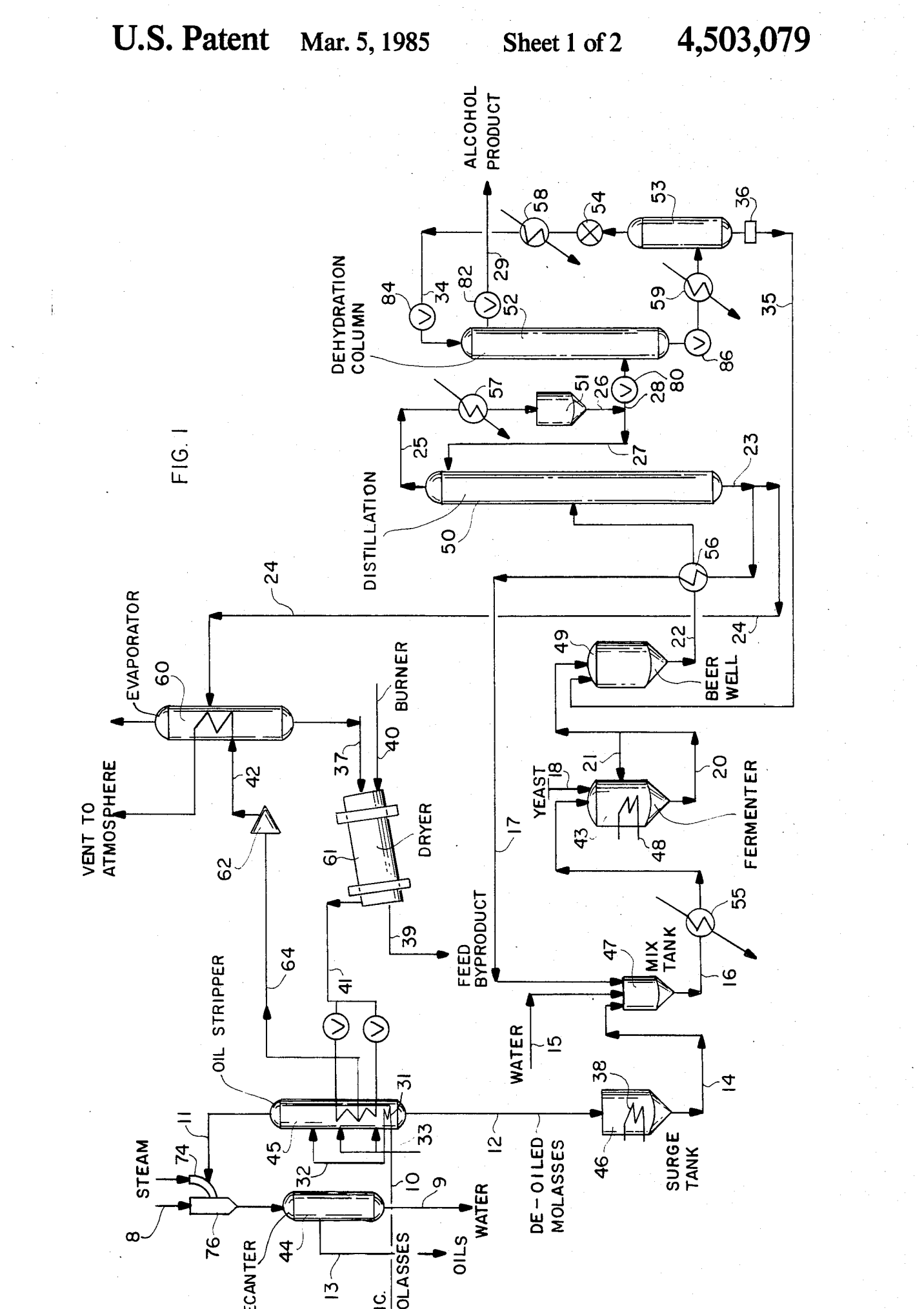
Figure 2:
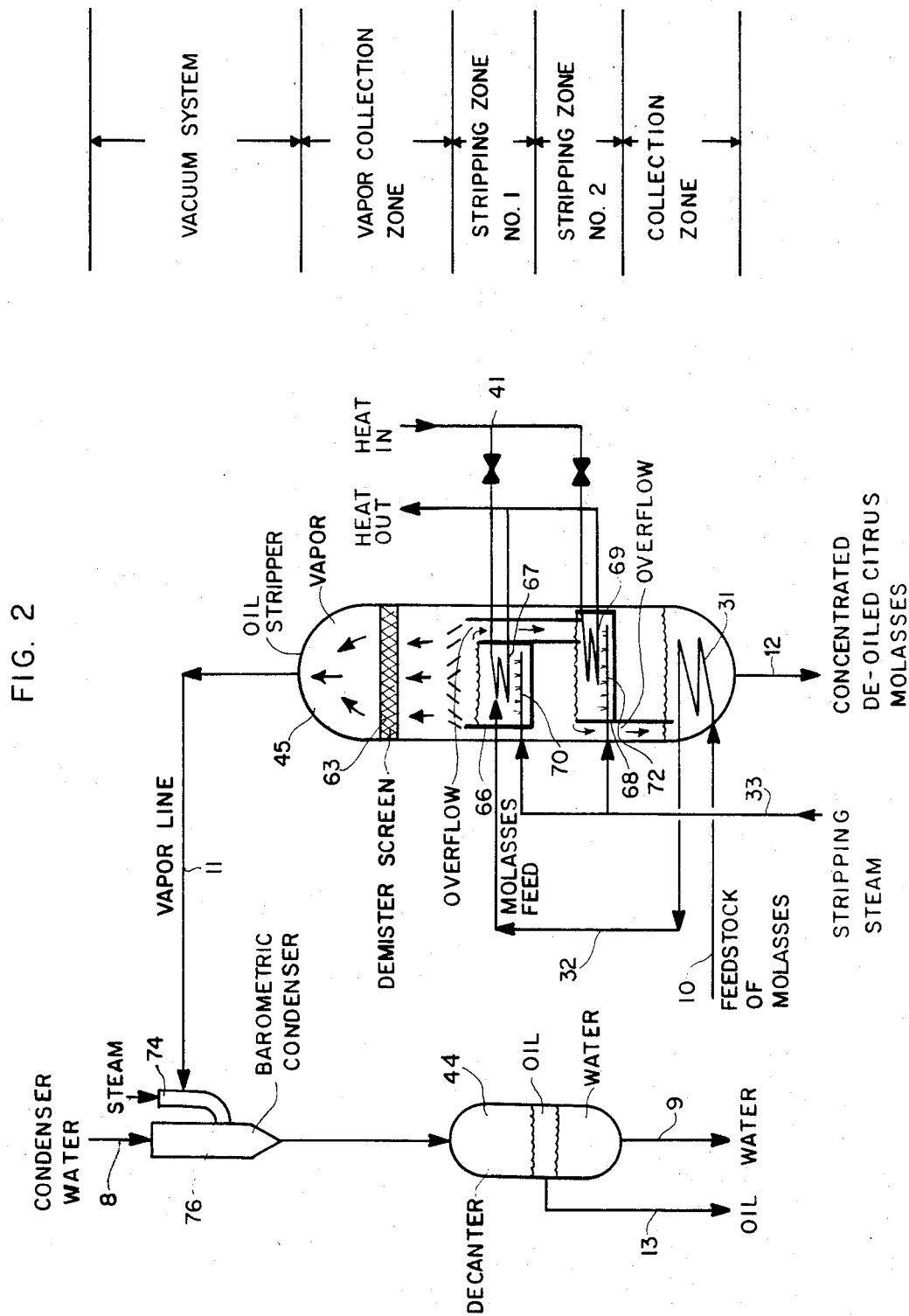
FIG. 2 is a showing, to a larger scale, of our novel oil stripper, along with the components with which it interacts.

With initial reference to FIG. 1, the process will now be described in greater detail.

A feedstock of citrus molasses typically 6° to 12.5° Brix and 80% to 90% moisture is introduced to the process through line 10. The citrus molasses is caused to pass through a coil 31 located in the lower portion of the oil stripper 45, where the citrus molasses is preheated. The preheated molasses is then transferred by line 32 to the upper portion of the stripper 45, where the essential oils, known as "stripper" oils, contained in the molasses are reduced from 0.2% to 0.5% concentration to less than 0.1% at approximately 240° F. to 260° F. The method of stripping preferred is to subject the heated molasses maintained at 5 to 10 psia with steam from line 33 sparged into controlled level trays to facilitate agitation of the molasses and to provide a motive force to carry away the vaporized oil and volatiles. The heat of vaporization is supplied from waste heat discharged from dryer 61 conducted through the stripper by means of line 41. This procedure will be discussed at greater length in connection with FIG. 2.

The action taking place in stripper 45 results in the vaporization of certain components, which vaporized materials are conducted from the stripper by line 11 leading to a steam jet ejector 74 that connects into the barometric condenser 76 which discharges into the upper part of the decanter 44. The steam jet creates a desired negative pressure in the stripper 45. The vapor is condensed by direct contact with water from line 8 in barometric condenser 76. The oils are then recovered by decanting in decanter 44 and are carried away from the system by line 13, for possible use in the creation of "scents" and the like. The condenser water is withdrawn from the decanter through line 9 for possible recycling to the system. Action in the decanter will be dealt with at greater length hereinafter.

The concentrated and de-oiled citrus molasses is at this time transferred from the stripper holding section via line 12 to process surge tank 46 which has the capability of cooling the liquid to prevent premature reactions from occuring during storage. For extended storage in the surge tank, a temperature of 55° F. to 60° F. is utilized to maintain the quality of the molasses. Well water may be circulated through a coil 38 located in tank 46, or water chilled by refrigeration means may be utilized.

The surge tank 46 permits a metered flow of the molasses to proceed to the system through line 14 to mix tank 47. The molasses is blended in the mix tank with 25% to 30% recycled process liquors supplied through line 17 cooled by heat exchanger 56, and 15% to 30% fresh water through line 15, facilitating a dilution of the molasses to 10° to 25° Brix, the most preferred for the economics of our process. The pH is adjusted to 4.0 to 5.5, with 4.5 being preferred, and the resultant mixture is highly fermentable to ethyl alcohol by yeast, preferably the yeast *Sacchromyces cerevisiae*.

The prepared molasses is transferred continuously through line 16 to heat exchanger 55 where the process stream is adjusted to a temperature of 85° F. to 95° F., and then delivered to fermenter 43 for fermentation. Yeast is introduced into fermenter 43 through line 18.

The heat exchanger 55 typically serves to cool the prepared mixture of molasses to the proper temperature for fermentation, for in the usual instance the mixture will be hotter than desired. However, when the molasses has been stored, and cooler molasses is encountered, steam (rather than water) would be circulated through the coils of the heat exchanger 55 in order to warm the molasses.

Cooling coils 48 are preferably utilized in the fermenter 43, with water from a well, or as an alternative, water or another suitable liquid used in conjunction with a cooling tower is utilized in order that a temperature suitable for the thriving of yeast cells will be maintained.

As will be seen hereinafter, some of our experimentation involved the use of ten 1,000 gallon fermentation tanks arranged in series, with overflow tubes drawing from the top of each preceding tank, and overflowing to the bottom of the following tank. Each tank had a turbine agitator to maintain dispersion of the yeast cell population. However, we found that this fairly elaborate arrangement was not required, but rather the number of fermenters employed is a function of individual economics rather than being a function of technology. For ease of description we have herein illustrated only a single fermenter 43.

To maintain a static condition in the fermentation reaction, after a population of yeast cells has been established, an amount of the fermentation stream equal to the incoming prepared process stream is removed continuously from fermentation through line 20 and is surged in beer well 49 for introduction to the distillation system. A portion of the fermentation liquid is recycled to the system through line 21 to insure adequate dispersion of active yeast cells and intimate contact with the substrate in the fermenter. The population of the yeast cells is able to attain much greater densities in this type of process than are attainable in typical batch systems and therefore the time of fermentation is less. By withdrawing and recycling a portion of the fermentation liquid containing yeast cells from the bottom of the fermenter 43, the accumulation of a dense unmoving mass of yeast cells in the bottom of the fermenter is avoided. The yeast population will be maintained healthy and active by the infusion of a small amount of fresh yeast to the fermenter periodically by way of line 18.

The beer (fermented material) is transferred from the beer well 49 through line 22 to heat exchanger 56, which pre-heats the beer to a temperature in the range of 120° F. to 125° F. while cooling, as previously mentioned, the recycled process water to say 100° F. to 110° F. The beer thus warmed is then introduced into the distillation system 50. The entire stream is subjected to distillation to maximize the recoverable yield of the product alcohol, which is ultimately to be removed at line 29.

The spent liquid stream containing the non-convertible materials, propagated yeast cells carried with the stream and water, is discharged from the distillation system at 215° F. to 225° F. through line 23. Whereas the portion of this stream flowing through line 17 is cooled, as mentioned above, and then recycled, the remainder of the stream is transferred through line 24 to evaporator 60 for the concentration and the recovery of the nutritional solids and non-volatile solubles. This stream is concentrated to a moisture of 40% to 60%.

The recovered concentrated stream is transferred from the evaporator 60 through conveyor 37 for drying in dryer 61. The dried product, containing 8% to 13% moisture is removed from the process by conveyor 39, and may thereafter be used as a feed byproduct, such as a feed for cattle.

The heat of drying is supplied by burner 40 and the waste heat vapor stream carried in line 41 is subsequently circulated through one, two or more coils in the oil stripper 45 for preparation of the incoming molasses. The vapor stream is thereafter conducted via line 64 to vapor recompressor 62, which is a turbine compressor or a like device, serving to compress the vapor stream to 30 to 35 psia, following which it is transferred through line 42 to a coil in the evaporator 60 such that the heat of compression of the waste heat vapor stream can be utilized as the primary heat source for the evaporator. The vapor vented from the evaporator could in some instances be conveyed into a like recompression system for further energy savings, by the reuse of heat within the system, instead of venting it to the atmosphere.

Referring now to FIG. 2, it will there be seen that we have illustrated a preferred embodiment of our novel oil stripper 45 in greater detail. As previously explained, the feedstock of liquid molasses is introduced to the system by means of line 10, whereupon it initially circulates through coil 31 in the lower part of the stripper 45, and is heated by the residual heat from the process contained in the partially concentrated molasses. The piping is continuous and unbroken, and the motive force of the incoming transfer pump will be sufficient to continue the flow through the coil 31 and into the stripper.

The pre-heated incoming molasses is then conducted by line 32 to controlled level tray 66, located in an upper interior portion of the stripper 45. The tray 66 is preferably made of stainless steel, and is equipped with a weir, such that the incoming molasses overflows at such time as a certain level is reached. Tray 68 is disposed in the stripper at a location below the tray 66, and is positioned to catch this overflow therefrom. Tray 68 is likewise equipped with a weir such that a continuous overflow takes place when a certain level is reached in tray 68, as more molasses is added. This overflow is collected in the bottom of stripper 45.

In order to apply heat necessary for the volatization of the oils contained in the citrus molasses, we prefer to utilize a pair of heat coils, such as a coil 67 in tray 66 and a coil 69 in tray 68. Although we can utilize steam from the plant boilers in these coils, we prefer to connect the line 41 emanating from dryer 61 to the coils such that the waste heat from the dryer can flow preferably downwardly through the coils as shown in FIG. 2, and play a predominant role in applying heat to the molasses contained in these trays. Suitable valves are provided such that the temperature of the trays can be maintained at a desired level, typically in the range of 240° F. to 260° F. A brix of approximately 30° in the first tray 66 is typical, and as a result of further volatization, a brix of 40° in the second tray 68 is normally expected. In some instances, we may prefer to use more than two trays, but in other instances only a single tray may suffice.

A plurality of steam nozzles 70 are disposed in a lower portion of tray 66, and a plurality of steam nozzles 72 are disposed in a lower portion of tray 68. Both sets of nozzles are connected to steam supply pipe 33, and as a result of this arrangement, steam is sparged into the molasses in these trays, not only to facilitate agitation of the molasses, but also to provide a motive force for carrying away the vaporized oil and volatiles.

A demister screen 63 is utilized in an upper part of stripper 45, which screen is a woven mesh of stainless steel wires. Its function is to provide a vast impingement surface for the precipitation of entrained droplets, as the vapors pass through its weaving.

As to the vapors carried away by the line 11, these are delivered to a steam jet ejector 74, which serves to create a desired negative pressure in the interior of the stripper 45. The negative pressure, preferably of 5–10 psia, induces a vaporization of components at a lower temperature than normal reducing heating requirements. The amount of negative pressure obtained will vary in accordance with the effectiveness of the stripping action.

The molasses overflowing from tray 68 of the stripper falls to the bottom of stripper, where it is retained in a holding section, which is also the location of coil 31 through which flows the incoming molasses feed that is to be preheated.

The citrus molasses is transferred by line 12 out of the holding section of the stripper, and delivered to surge tank 46, as previously explained.

After passing through the steam jet ejector 74, the vaporized materials are condensed by a barometric condenser system 76, which is a commercially available device made for example by the Croll-Reynolds Company. The device 76 is located above decanter 44 in order to take advantage of the force of gravity acting upon the condensing water and condensed vapors.

As will be noted from FIG. 2, the oils collect atop the water residing in the bottom of the decanter 44, and these oils are decanted off and removed by line 13 to a location for the further processing thereof. As previously mentioned, the water removed via line 9 may be recycled to the system.

Returning now to FIG. 1, the distillation system preferably is of sieve tray design and the stripping section, located in the lower portion of vessel 50, is designed to handle the total incoming beer stream, including yeast cells protein fiber, ash, soluble and insoluble materials that comprise the byproduct feed materials. The rectifying section of the distillation system, located in the upper portion of vessel 50, can be of any suitable distillation design to accomplish binary distillation of ethanol and water.

Distillation may be conducted in typical fashion, well known to the industry. The alcohol produced from the distillation system is approximately 190° proof and is transferred in vapor state through line 25, typically at 173° F. to 180° F., to heat exchanger 57 and subsequently to reflux tank 51.

The heat exchanger 57 located in line 25 serves as a condenser of the alcohol vapors that are present at this point in the process, and water is preferred as the exchange medium. This condensing function also serves to induce a slight negative pressure on the system to facilitate a controlled flow of vapors from the process.

The product alcohol stream is now transferred from the reflux tank 51 through line 26, and a portion of the alcohol is recycled in typical fashion through line 27 to serve as the reflux liquid for the distillation system. The remainder of the product alcohol is transferred through line 28, past valve 80, to the dehydration column 52.

The dehydration column is filled with a molecular sieve (a crystalline metal alumino silicate), an adsorbent material with an affinity for water. This material, which has a catalytic action, is available from W. R. Grace Co. and from Union Carbide. Other sources for satisfactory material of this general type are Ad-Pro of Tyler, Tex., and Anhydrous Technology, Inc. of Big Spring, Tex. The product alcohol of approximately 190° proof is contacted with the molecular sieve in liquid state at 80° F. to 95° F. The water is retained in the molecular sieve 52, whereas the anhydrous ethyl alcohol is recovered through line 29 as the final product. During normal operation, valves 80 and 82 are open, so as not to inhibit alcohol flow, whereas valves 84 and 86 would be closed.

It is to be noted that we are not to be limited to the above-mentioned method of dehydrating the ethanol, for we may also use a more conventional approach of azeotropic distillation using benzene or cyclohexane or a like material as the ternary substance. Also we may use metallic salts in a chemical absorption process, or use a glycol solution in an extractive distillation process.

After normal operation has proceeded for a number of hours, a point will be reached at which the molecular sieve material will have received its capacity of water, and no further entrained water will be able to be removed from the product alcohol. At this point, the molecular sieve will need to be regenerated, i.e., the catalyst will need to be purged of water before it can again be effective. We prefer to regenerate the molecular sieve catalyst by a closed loop nitrogen backwash system. This system principally includes nitrogen surge tank 53, a blower 54, heat exchanger 58, and on the far side of the dehydration column, the heat exchanger 59. As will be noted from FIG. 1, valve 84 controls the flow of nitrogen into the dehydration column 52, and valve 86 controls the exit of nitrogen from the column.

Thus, as needed, the molecular sieve is purged of the retained water and residual alcohol by a backwash system, using nitrogen during a pre-determined interruption of the ethyl alcohol flow. As is obvious, the valves 80 and 82 would be closed at that time. It is to be realized that the molecular sieve catalyst has a specific capacity to adsorb water from the process alcohol stream, depending on the proof of the incoming alcohol and the flow rate. The higher the proof of the alcohol, the longer the sieve can operate without regeneration.

Nitrogen under pressure is contained in vessel 53, and it is compressed by a blower 54 or similar device to 20 to 25 psia and 175 to 185 cfm, and heated to a selected temperature by heat exchanger 58. The heated, pressurized nitrogen becomes the heated medium for the regeneration cycle, although it should be noted that preliminarily, unheated nitrogen may serve as a pressure purge to blow the free liquid (alcohol and water) that is contained in the void areas of the catalyst bed out of such bed, as the initial stage of regeneration. The free liquid is conducted through heat exchanger 59, where the nitrogen and entrained liquid are cooled, with this facilitating precipitation of the entrained liquid from the nitrogen.

We prefer to use two distinctly different temperature phases insofar as regeneration is concerned. At an initial low temperature, nitrogen flow into the dehydration column 52 via line 34 serves to heat the catalyst slowly, which is desirable. Typically, the nitrogen during this initial phase is in the temperature range of 125° F. to 140° F., with 140° F. being preferred. In this way, thermal shock is prevented, thus avoiding possible destruction of the integrity of the catalyst structure.

For complete regeneration of the catalyst, it is thereafter necessary to vaporize the adsorbed moisture from the pores of the catalyst, utilizing relatively high temperatures. Thus, after the catalysts has been warmed sufficiently, the nitrogen stream is then heated to a temperature in the range of 425° F. to 460° F., with 450° F. being preferred.

So that these two distinct phases can be accomplished, the heat exchanger 58 is preferably an electric heater that can be operated in at least two different temperature regimes, such as by suitable modification of the supply voltage to the heat exchanger. It typically operates at a gage pressure of approximately 5 psi.

As should now be apparent, heated, pressurized nitrogen is the medium preferred for the regeneration cycle, and it is conducted by line 34 into the dehydration column 52 countercurrent to the direction of the ethyl alcohol processing flow. The surface water and retained alcohol are purged from the system by the pressurized flow of nitrogen, are cooled by heat exchanger 59, and separated from the nitrogen stream in tank 53, which may be regarded as a nitrogen surge tank. The recovered ethanol and water are removed from the system by standard pressure system liquid trapping devices, and are conducted by line 35 to beer well 49 for reprocessing in the distillation system. Preferably, the integrity of the pressure of the nitrogen system will be maintained and the liquid properly separated by the use of a condensate trap 36 mounted in line 35 adjacent the tank 53. The device 36 is of a commercially available type.

We have found that a typical operation involved six hours of alcohol production followed by approximately eighteen hours of recycling of the nitrogen through the above-described closed loop, such that regeneration of the catalyst can be accomplished. However, we obviously are not to be limited to these values.

For the further understanding of the invention, the following examples are given.

EXAMPLE 1

A dilute solution of citrus molasses with a Brix of 10° and a moisture and volatiles content of 90%, a solids content of 10% and an oil content of 0.35% was subjected to a temperature of 250° F. and the evolved vapors were drawn away and condensed by a condenser. The recovered citrus molasses solution with a Brix of 40° and a moisture and volatiles content of 58.5% and a solids content of 41.4% and an oil content of 0.091% was collected and cooled to 88° F.

3,189 lbs of stripped citrus molasses was diluted with 1,749 lbs of recycled process water with a Brix of 5° and a moisture and volatiles content of 92.1% and a soluble and insoluble solids content of 8.0% and an oil content of 0.087% and with 1,143 lbs of water. The blended solution with a Brix of 20° and a moisture and volatiles content of 76% and a solids content of 3.7% and an oil content of 0.09% and a pH of 4.5 was treated with 2 lbs of the yeast *Sacchromyces cerevisiae*.

Fermentation began within 2 hrs and was completed within 48 hrs. The tendency of the citrus molasses to foam was controlled by adding anti-foaming agents.

5,585.5 lbs of fermented material was recovered and distilled, producing 602.2 lbs of ethanol at 190° proof and 4,983.3 lbs of residual material with a moisture and volatiles content of 92.1% and a soluble and insoluble solids content of 8.0%.

The residual material was dried and on a dry material basis consisted of 13.44% crude protein (containing 10.49% digestible protein), 1.51% crude fiber, 64.52% nitrogen free extract, 9.49% ash and 11.01% crude fat. Total digestible nutrients are 87.09%.

EXAMPLE 2

A dilute solution of citrus molasses with a Brix of 10° and a moisture and volatiles content of 90% and a solids content of 10% and an oil content of 0.35% was subjected to a temperature of 250° F. and the evolved vapors were drawn away and condensed by a condenser.

The recovered citrus molasses solution with a Brix of 40° and a moisture and volatiles content of 58.5% and a solids content of 41.4% and an oil content of 0.091% was collected and cooled to 85° F.

1,864 lbs of stripped citrus molasses was diluted with 4,581.5 lbs of water. The blended solution with a Brix of 12° and a moisture and volatiles content of 77.9% and a solids content of 2.0% and an oil content of 0.03% and a pH of 5.8 was treated with 2 lbs of the yeast *Sacchromyces cerevisiae*.

Fermentation began within 2 hrs and was completed within 48 hrs. The tendency of the citrus molasses to foam was again controlled by anti-foaming agents.

6,315.5 lbs of fermented material was recovered and distilled, producing 170.6 lbs of ethanol at 190° proof and 6,144.9 lbs of residual material with a moisture and volatiles content of 93.41% and a soluble and insoluble solids content of 6.6%.

The residual material was dried and on a dry material basis consisted of 17.07% crude protein (containing 13.31% digestible protein), 1.21% crude fiber, 54.4% nitrogen free extract, 15.47% ash and 11.83% crude fat. Total digestible nutrients are 82.71%.

EXAMPLE 3

Ten 1,000 gallon capacity fermentation tanks were arranged in series with overflow tubes drawing from the top of the preceding tanks and overflowing to the bottom of the following tanks, each tank having a turbine agitator to maintain dispersion of the yeast cell population.

2,525 lbs per hour of substantially oil stripped fermentable citrus molasses substrate was introduced into the three tanks and a yeast population was allowed to develop. After 12 hours of yeast propagation and of active fermentation, the feedstock was again introduced to the system at the rate of 2,525 lbs per hour.

To maintain a static condition in the system, liquid was removed at the rate of 2,323 lbs per hour.

Steady state flow resulted in a fermented materials stream with 8.7% solids and 8.1% alcohol and 83.2% moisture.

EXAMPLE 4

1,660 gallons of ethanol and water were introduced to the molecular sieve column, with a composition of the ethanol and water mixture of 10,345.0 lbs ethanol and 691.4 lbs water, at a flow rate of 4.5 gpm and a temperature of 85° F.

Flow was maintained for 6.16 hours with a resulting production from the vessel of 1,000 gallons with a composition of 6,549.5 lbs ethanol and 13.33 lbs water for a proof reading of 199.68°.

660 gallons were retained in the column.

The column was pressurized with nitrogen at 135° F. and the retained liquid was blown to the feed tank. 561 gallons were recovered for recycle with a proof reading of 191.1°.

The nitrogen flow as heated to 450° F. and continued purging of the molecular sieve column was conducted. The vaporized water and ethanol were condensed resulting in the recovery of 85.8 gallons of ethanol and water with a proof reading of 112° for reprocessing.

In this particular instance, the regeneration of the molecular sieve catalyst was conducted for 23.0 hours. The catalyst was completely regenerated in 18 hours, and we found that the additional time of regeneration provided no additional benefit.

What is claimed is:

1. A process for producing a fermentable feed stock from citrus molasses by removing certain inhibiting substances, including essential oils, that serve to inhibit fermentation, comprising heating citrus molasses containing inhibiting substances to a temperature of at least 240° F. in a stripping zone to volatilize off a substantial amount of the inhibiting substances, and then fermenting the stripped citrus molasses with yeast to produce a fermented product containing ethyl alcohol.

2. The process of claim 1 in which the steam stripping step is carried out at a temperature of about 240° to 260° F. to effectively remove substantial amounts of essential oils.

3. A process for improving the yield of ethyl alcohol in the fermentation of citrus molasses, by removing certain inhibiting substances, including essential oils, that inhibit such fermentation, comprising the steps of stripping a substantial percentage of the fermentation inhibiting substances from the citrus molasses, by heating to a temperature of at least 240° F., conducting the stripped citrus molasses to a fermentation zone, adding water and at least a portion of recycled process liquor to produce a beer mixture, fermenting the beer mixture in the presence of yeast to produce a substantial yield of ethyl alcohol, passing the fermented, alcoholic mixture to a distillation zone, distilling and condensing the alcoholic component from the fermented mixture, resulting in a byproduct process liquor, and thereafter recycling a portion of the process liquor to a mix tank in the fermentation zone.

4. In the process of claim 3, wherein an unused portion of the process liquor is dried to produce an animal feed.

5. The process of claim 3, in which the alcoholic component from the distillation step has a proof of about 190°.

6. The process of claim 3 in which the alcoholic component is dehydrated in the presence of a molecular sieve.

7. The process of claim 3, in which the process of fermentation and distillation is carried out continuously.

8. A process for improving the yield of ethyl alcohol in the fermentation of citrus molasses, by removing certain inhibiting substances, including essential oils, that inhibit such fermentation, comprising the steps of stripping a substantial percentage of the fermentation inhibiting substances from the citrus molasses by heating to a temperature of at least 240° F., conducting the stripped citrus molasses to a fermentation zone, adding water to produce a beer mixture, fermenting the beer mixture in the presence of yeast to produce a substantial yield of ethyl alcohol, passing the fermented alcoholic mixture to a distillation zone, and distilling and condensing the alcoholic component from the fermented mixture.

* * * * *